United States Patent [19]

Ransford et al.

[11] Patent Number: 5,490,221
[45] Date of Patent: Feb. 6, 1996

[54] DIGITAL DATA REGISTRATION AND DIFFERENCING COMPRESSION SYSTEM

[75] Inventors: Gary A. Ransford, New Orleans; Vivien J. Cambridge, Slidell, both of La.

[73] Assignee: The United States of America as represented by the Administrator of the National Aeronautics and Space Administration, Washington, D.C.

[21] Appl. No.: 842,956

[22] Filed: Feb. 28, 1992

Related U.S. Application Data

[63] Continuation-in-part of Ser. No. 591,643, Oct. 2, 1990, abandoned.

[51] Int. Cl.$^6$ .................................................. G06K 9/00
[52] U.S. Cl. ........................ 382/130; 382/236; 382/215; 382/132; 364/413.23; 364/413.14
[58] Field of Search .................................. 382/6, 56, 130, 382/236, 238, 215, 132; 358/448; 395/120, 125; 364/413.13, 413.14, 413.23; 250/370.08, 370.09

[56] References Cited

U.S. PATENT DOCUMENTS

| | | | |
|---|---|---|---|
| 3,905,045 | 9/1975 | Nickel | 444/1 |
| 4,533,947 | 8/1985 | Smith | 358/111 |
| 4,635,293 | 1/1987 | Toshiba | 382/44 |
| 4,644,582 | 2/1987 | Morishita et al. | 382/6 |
| 4,685,146 | 8/1987 | Fenster et al. | 382/54 |
| 4,692,878 | 9/1987 | Ciongoli | 382/47 |
| 4,742,558 | 5/1988 | Ishibashi et al. | 382/56 |
| 4,802,093 | 1/1989 | Ema | 364/413.23 |
| 4,809,350 | 2/1989 | Shimoni et al. | 382/56 |
| 4,935,879 | 6/1990 | Ueda | 382/28 |
| 4,945,478 | 7/1990 | Merickel et al. | 382/6 |
| 5,056,524 | 10/1991 | Oe | 364/413.23 |
| 5,151,795 | 9/1992 | Adachi | 382/6 |
| 5,151,856 | 9/1992 | Halmann et al. | 364/413.13 |
| 5,175,806 | 12/1992 | Muskovitz et al. | 395/125 |
| 5,175,808 | 12/1992 | Sayre | 395/125 |

*Primary Examiner*—Leo Boudreau
*Assistant Examiner*—D. R. Anderson
*Attorney, Agent, or Firm*—Robert L. Broad, Jr.

[57] ABSTRACT

A process for X-ray registration and differencing results in more efficient compression. Differencing of registered modeled subject image with a modeled reference image forms a differenced image for compression with conventional compression algorithms. Obtention of a modeled reference image includes modeling a relatively unrelated standard reference image upon a three-dimensional model, which three-dimensional model is also used to model the subject image for obtaining the modeled subject image. The registration process of the modeled subject image and modeled reference image translationally correlates such modeled images for resulting correlation thereof in spatial and spectral dimensions. Prior to compression, a portion of the image falling outside a designated area of interest may be eliminated, for subsequent replenishment with a standard reference image. The compressed differenced image may be subsequently transmitted and/or stored, for subsequent decompression and addition to a standard reference image so as to form a reconstituted or approximated subject image at either a remote location and/or at a later moment in time. Overall effective compression ratios of 100:1 are possible for thoracic X-ray digital images.

16 Claims, 10 Drawing Sheets

\* Spatial adjustment of images to correct location, scale, and orientation differences

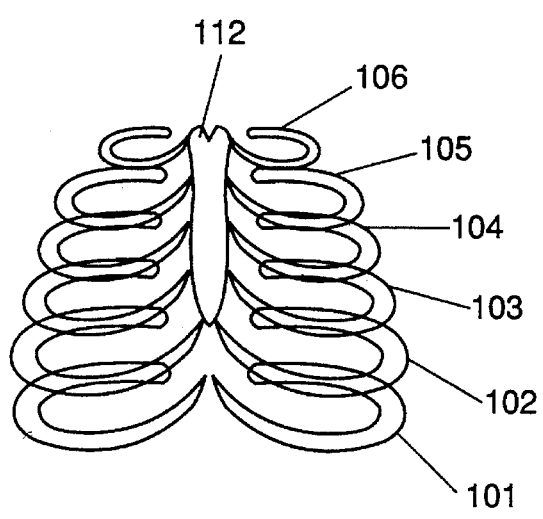 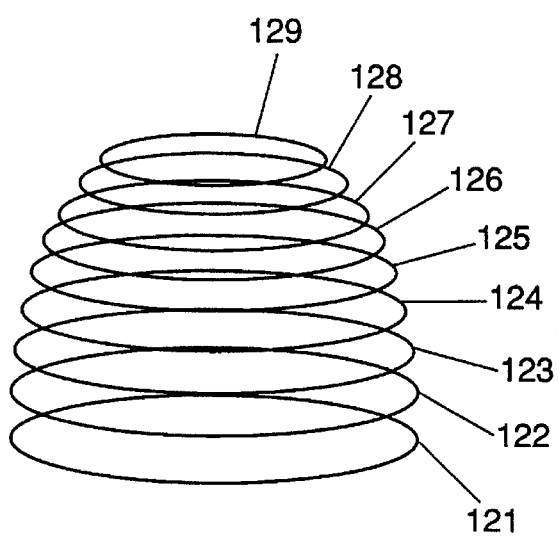
Fig. 7A  Fig. 7B

DIGITAL DATA REGISTRATION AND DIFFERENCING COMPRESSION SYSTEM

ORIGIN OF THE INVENTION

The invention described herein was made in performance of work under a NASA contract, and is subject to the provisions of Section 305 of the National Aeronautics and Space Act of 1958, Public Law 85-568 (72 Stat. 435; 42 U.S.C. §2457). This is a continuation-in-part application of application Ser. No. 07/591,643 filed Oct. 2, 1990, and now abandoned, in the names of Gary A. Ransford and Vivien J. Cambridge for "DIGITAL IMAGE DIFFERENCING FOR STORAGE AND TRANSMISSION OF X-RAY IMAGERY"

BACKGROUND OF THE INVENTION

This invention generally concerns a digital data processing system capable of reducing transmission time and storage requirements, and particularly concerns compression and subsequent decompression of digital data images, such as X-rays, which are inherently similar in many respects; and, wherefore, a priori knowledge of such images can be used in their compression.

Although the preferred areas of application (and the following discussion of background and description) of the invention pertain mainly to the medical and teleradiological fields, similar problems as discussed herein exist in other similar systems which deal with the compression and storage of large amounts of digital data; accordingly, advantages and benefits of this invention are equally applicable to such other systems. With such an understanding, it should be appreciated that the following discussion of specific exemplary present embodiments is in no way meant to limit the scope of the present invention to strictly medical applications.

Electronic transmission of various types of digital data, in particular radiological data (teleradiology), involves the transmission of a tremendous volume of data. Unless expensive broadband systems are used, such high data volume causes the transmission process to be relatively slow, and with the quality of the transmitted image often deteriorated. In the case of teleradiology, the transmission time is crucial for prompt analysis of a patient's condition and the sharing of analytical expertise between hospitals, clinics, and the like.

State of the art radiological systems produce digital imagery which may contain one megabyte of data per image. Since there is information throughout the frame, systems which attempt to transmit for example chest X-rays must process the entire volume of image data. Because of such large volume of data, most systems include relatively expensive image compression schemes. The efficiency of compression can be measured by the ratio of the necessary storage size before compression to the necessary storage size after compression (compression ratio). However, the compression algorithms incorporated in such schemes rarely achieve compression ratios greater than 5:1. State of the art image transmission systems incorporating conventional image compression and using 9600 baud telephone lines still require more than six minutes for the transmission of one 1024×1024 image.

Storage of the imagery data is also a problem. One uncompressed image requires approximately one megabyte of storage space, obviously necessitating considerable storage capability to maintain a library of any significant number of different digital images.

Various forms of digital image differencing for image compression and digital image differencing for image enhancement are known. However, such differencing methods of the prior art do not provide features and advantages of the present invention.

Methods which perform differencing for image enhancement generally aim to enhance images by removing contrast detail information which is similar in the images. In such cases, the information in the difference image is typically presumed to be diagnostically interesting. The difference image contains sharply reduced intensity values in the regions where the contrast detail of the original images was similar, and normal intensity values in the regions where there were appreciable differences. Hence, contrast between such forms of difference information and the background is enhanced. Such prior method of image enhancement is often used in medical imaging to examine changes in the medical condition of specific parts of anatomy or to visualize vessels and cavities by subtracting images taken before and after some tracer element is injected (e.g., Digital Subtraction Angiography).

The difference image obtained with the foregoing often contains less contrast detail than the original images. At a minimum, if the original images were similar, the intensive values of most pixels in the difference image are low. This, however, does not mean that the size of the difference image (i.e., the volume of data) is smaller than that of the original image. Indeed, a difference image which entirely comprises eight bit, low intensity pixels is as large as an original image which contain the same number of eight bit pixels, but which displays maximum contrast detail.

U.S. Pat. No. 3,905,045 to Nickel concerns an apparatus for image processing using a plurality of operations in sequence to produce a difference image, including bilinear mapping of one image on the other to register the images and photoequalization to generate a difference image. Image warp transformation is disclosed using operator selected match points on a pair of images, along with an image correlation process using a second group of matching points. The size of the differenced image is, however, as large as either of the two original images, wherefore no compression is achieved.

U.S. Pat. No. 4,533,947 to Smith discloses a method for increasing the data storage transfer rate in a system to permit the recording of a rapid sequence of high resolution images by eliminating designated portions of each image in the sequence. The disclosed method operates on the premise that two images which are related, particularly through temporal continuity, have similar intensity values over a significant portion of the pixel matrix. Portions of the image where pixel values have not changed beyond some threshold from corresponding portions in a related image are recognized, and those image portions where significant change is indicated are transmitted. A high degree of spatial correlation is assumed between the image matrices before they enter the system. The method does not accommodate situations in which images do not match because of differences such as in orientation, location, gray scale intensity range, and scale of component elements. Such may be typical whenever images are not recorded in rapid sequence.

U.S. Pat. No. 4,742,558 to Ishibashi et al. discloses a method for the reduction of codes necessary to display a designated image area contained in a global image. An original image is represented by a hierarchical structure from a global image of high level to a local image of low level. Only difference information between the images of the respective levels is coded and stored so that the number of codes will not be increased. The method includes a step in which differencing of image data takes place, but one image is not differenced from another relatively unrelated image. Rather, the image is compared to and differenced from itself. The objective is apparently not to reduce image data but to reduce the cost of splitting the image into several levels of a hierarchical structure according to different resolutions of the image.

U.S. Pat. No. 4,802,093 to Ema discloses an X-ray image processing apparatus which performs image differencing and gray scale transformation to reduce the gray scale differences between images prior to differencing. The invention relates to image enhancement by digital differencing such as Digital Subtraction Angiography (DSA). The system transforms the gray scales of the respective images to minimize the total intensity difference between them. This results in a difference image whereby the background to the contrast enhanced areas has lower intensity values, making the contrast enhanced areas more visible.

U.S. Pat. No. 4,809,350 to Shimoni et al. discloses an image compression system which mathematically approximates the image function and defines the difference image as the difference between the image and the approximating model. An image is used to predict itself and the model is subsequently used in the differencing operation. Although steps of acquisition, image subtraction, compression, storage, decompression, and image addition are disclosed, the differencing method is fundamentally different from the present invention. Shimoni et al. is inherently limited as an effective system because, for example, it uses an inherently related image in the subtraction process, while the present invention advantageously makes use of a relatively unrelated reference image. The fact that the images of the present invention are not inherently related allows greater flexibility and higher compression ratios as explained in the DETAILED DESCRIPTION OF THE PREFERRED EMBODIMENTS.

U.S. Pat. No. 4,685,146 to Fenster et al. discloses a method for correcting for artifacts generated by object-motion caused misregistration between different images. Enhancement is provided through image differencing, and in particular a method is disclosed for assuring valid registration of images to be compared to obtain image enhancement with minimal artifacts.

U.S. Pat. No. 4,635,293 to Watanabe and U.S. Pat. No. 4,644,582 to Morishita et al. also generally disclose various methods for image registration and alignment.

SUMMARY OF THE INVENTION

The present invention recognizes and addresses various of the foregoing problems and shortcomings, and others, concerning digital imagery generally. This invention more particularly addresses the expense and time required for the transmission and/or storage of an image containing a large volume of digital data, especially in the field of teleradiology. Accordingly, it is one principal object of the present invention to provide an improved method for digital image compression which reduces transmission time and/or storage requirements. It is an additional object to provide for effective decompression of the transmitted and/or stored data.

A further object of the present invention is to provide a method which makes more efficient and effective use of present conventional compression algorithms.

It is also an object of the present invention to provide a method that enables separation and amplification of diagnostically significant data contained in a larger image, thereby providing a useful diagnostic tool.

Another object of the present invention is to provide method of image compression that achieves a far greater overall compression ratio than conventional compression systems.

Yet another object of the present invention is to provide a method of producing an image that is less severely distorted by potent compression algorithms, thereby allowing for stronger compression tools.

Another principal object of the present invention is to provide a method whereby relatively insignificant data can be edited from a subject image prior to compression yet still be represented in the final approximation of the same subject image.

Still another object of the present invention is to provide an effective differencing and compression system capable of use for relatively unrelated and uncorrelated images.

Additional objects and advantages of the invention will be set forth in part in the description which follows, and in part, will be obvious from the description or may be learned by practice of the invention. The objects and advantages of the invention may be realized and attained by means of the instrumentalities and combinations pointed out in the appended claims.

Also, it should be appreciated that modifications and variations to the specifically illustrated and discussed features and steps hereof may be practiced in various embodiments and uses of this invention without departing from the spirit and scope thereof, by virtue of present reference thereto. Such variations may include, but are not limited to, substitution of equivalent steps and features for those shown or discussed, and the functional or positional reversal of various steps, or the like, where no substantial change to the present invention results.

Still further, it is to be understood that different embodiments, as well as different presently preferred embodiments, of the present invention may include various combinations of presently disclosed features, steps, or their equivalents (including combinations thereof not expressly shown or stated).

To achieve the present objects and in accordance with the purpose and spirit of the invention as embodied and broadly described herein, one exemplary method of the present invention for the compression of digital imagery data comprises the steps of: obtaining a subject image containing digital imagery data; modeling the subject image upon a three-dimensional model to provide a modeled subject image; performing registration of the modeled subject image with a modeled reference image obtained from modeling a relatively unrelated standard reference image upon the three-dimensional model, so that the modeled subject image and modeled reference image are translationally correlated, with resulting correlation of the modeled images in spatial and spectral dimensions; differencing the modeled reference image and the modeled subject image to form a differenced image; and compressing the differenced image to provide a compressed differenced image.

The invention is applicable generally to any situation where a large volume of data is desired to be transferred at high speed; accordingly, it is within the scope and spirit of the present invention to include all such applications or the teachings hereof. Although radiography and X-rays will be discussed in describing the invention, it should be understood that such is for the purpose of disclosing present preferred embodiments and not for limiting the scope of the invention to one area.

The subject image may be formed with one of any known type of digital imagery, for example X-rays, and preferably, obtaining the subject image can be by way of any known conventional method, for example, use of digital radiographic systems.

Presently disclosed interactive editing of the subject image preferably comprises identifying an area of interest on the subject image through operator selection. In one alternative embodiment, such editing may be accomplished automatically by computer identification of a predetermined area of the subject image (such as based on "advance" operator selection through programming). This may be accomplished by gray scale value discrimination, pixel contrast intensity, pixel location, or any other applicable method.

In one preferred embodiment, interactive editing is accomplished by an operator viewing the subject image and designating the area of interest. For example, the operator may view a subject image upon a CRT screen and designate the area of interest such as through use of a light pencil.

The modeling operation correlates the subject image to the model so that the three-dimensional representation of the depicted thorax is said to fit the model. The subject image is correlated to the model; the model is not correlated to the subject image.

In one preferred embodiment of the present invention, modeling features include an image warping operation which emulates three-dimensional transformation. The image warping operation may employ known image warping algorithms to transform the two-dimensional subject image into a three-dimensional representation of itself and back into a two-dimensional modeled image with reassigned pixel values corresponding to the three-dimensional representation.

In a further embodiment of the present invention, the three-dimensional model comprises a computer-generated model representative of a component element common to the subject image and the reference image.

In yet another embodiment of the invention, the standard reference image is capable of being correlated with subject images originating from more than one source. For example, a single standard reference image can be correlated with a subject image from sources A, B, or C. There is no necessity that a reference image be compatible with only subject images from one source, or that the reference image itself originates from the same source as the subject image.

In a further, alternative preferred embodiment, a region smoothing operation may be applied to the difference image to decrease noise therefrom.

In one embodiment of the invention, the compression of the differenced area of interest is accomplished with conventional compression algorithms, so as to allow for more efficient use of the algorithms resulting in relatively greatly increased compression ratios over prior usage of the same algorithms.

In accordance with yet a further alternative feature of the invention, an enhanced intermediary storage capability may be provided whereby the differenced image can be stored for subsequent recall and decompression thereof. Such intermediary storage capability can be provided at the situs of compression prior to any data transmission, at a receiving station prior to decompression, or at some intermediary storage facility.

To further achieve present objects and in accordance with purposes of the invention, as embodied and broadly described herein, there is provided a method for the effective compression and transmission of radiographic imagery exploiting prior known information of the image. Such method comprises first obtaining a subject X-ray which contains data of relative diagnostic importance. The subject X-ray is then modeled upon a three-dimensional model representative of a particular element contained in the subject X-ray to provide a modeled subject X-ray. The modeled subject X-ray is registered with a modeled reference X-ray which is obtained by modeling a relatively unrelated standard reference X-ray upon the same three-dimensional model as the subject X-ray was modeled upon. Such standard reference X-ray preferably comprises the relative equivalent of the subject X-ray without the diagnostically important data. Interactive editing of the subject X-ray results in operator selection of an area of interest encompassing at least the diagnostically important data.

With the foregoing steps, the modeled images, by being modeled upon the same three-dimensional model, are translationally correlated during the registration operation to provide for correlation of the modeled images in spatial and spectral dimensions. After being so registered, the modeled subject X-ray and the modeled reference X-ray are differenced, providing a differenced X-ray which includes the previously identified area of interest. The difference X-ray is (optionally) subsequently reduced to eliminate undesired portions therefrom which further significantly reduces the amount of data to be compressed, such reduction (if practiced) providing a reduced differenced X-ray including at least the area of interest. Enhanced compression of at least the area of interest of the differenced X-ray (after reduction, if practiced) provides a compressed differenced X-ray.

The compressed differenced X-ray may then be transmitted if desired to a predetermined receiving station so that the compressed area of interest can be subsequently decompressed for addition to a duplicate of the standard reference X-ray. Such addition yields a relatively precise approximation of the original subject image. Alternatively to transmission, local storage may be practiced with the same subsequent decompression/addition operations available for image recall function.

In another preferred embodiment of the invention, the three-dimensional model comprises a computer-generated model of a human thorax with the subject and reference X-rays being modeled thereupon.

In yet another preferred embodiment of the invention, the subject X-ray comprises a chest X-ray and the standard reference X-ray comprises a "healthy" chest X-ray without diagnostically important data. Preferably, the standard reference X-ray is compatible with subject X-rays originating from various sources and is not restricted to use with subject X-rays originating from the same source.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIGS. 7-10 illustrate the modeling process, with FIG. 7A illustrating an image of a thorax to be modeled.

FIG. 7B shows a stack of ellipses which can be the basis used for the modeling process.

FIG. 8 is a view showing how grid lines and the ellipses of FIG. 7B define the model on which the subject and reference images are modeled.

FIG. 9 is a view showing the image of the thorax superimposed on the model.

Figure 1:
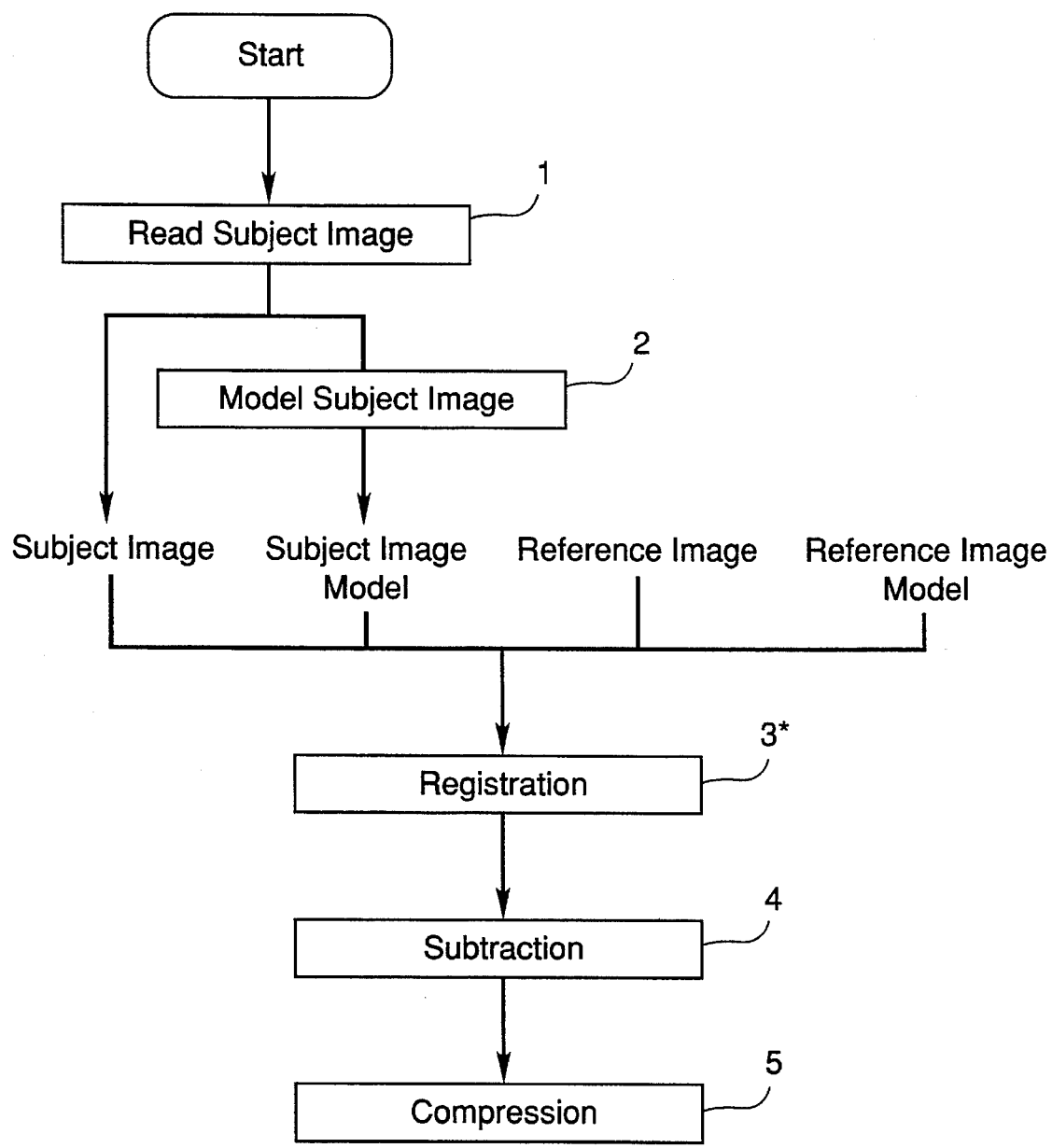
FIG. 1 is a block diagram overview of one preferred exemplary embodiment of the method of the present invention.

Repeat use of reference characters throughout the present specification and appended drawings is intended to represent same or analogous features or aspects of the invention.

DETAILED DESCRIPTION OF THE PREFERRED EMBODIMENTS

Reference will now be made in detail to the present preferred embodiments of the invention, examples of which are illustrated in the accompanying drawings. Those of ordinary skill in the art will appreciate that the following disclosure is for purposes of example only, and is not intended to limit broader aspects of the invention referenced thereby.

Broadly speaking, the method of the present invention for the effective compression (and optional transmission) or digital imagery data exploits prior known information of an image. The method makes use of the fact that images are inherently similar and that therefore, a priori knowledge of the images can be used in their compression. Such technique allows subtraction of two images, for example, one standard "healthy" image and one containing data of relative diagnostic significance, including correction for differences in orientation and geometry of the features contained in the images before subtraction. The image which remains after subtraction comprises information due to the differences between the images. It is this difference information caused by the diagnostically significant data that is potentially meaningful and which desirably should be preserved for storage and/or transmission.

Present FIG. 1 discloses in general block diagram format a first presently preferred embodiment of this invention. The illustrated steps are represented in a specific sequence, and generally disclose the minimum necessary steps for achieving the present goal of image compression through differencing of images which are spatially relatively uncorrelated (i.e., the subject image and the reference image). The illustrated system correlates the images through a process which spatially adjusts X-ray images of preferably a human thorax by a two-dimensional image warping operation which emulates three-dimensional transformations of the thorax. Such procedure results in corrected differences for location and scale of the thoraxes, as well as for relatively small or minor orientational differences. it is particularly advantageous that the system presently represented allows the images involved in the substraction process to be relatively uncorrelated. The resulting system is applicable because of such features to general teleradiology and digital image storage applications.

In addition, the fact that the two above-described images are acquired separately and independently from one another allows the method to optionally compress and store only a small, interactively identified region of interest. The remainder or complementary portion of the image may be replaced with image data similar to it in a final step, i.e., whenever the difference image is added back to the reference image.

Referring more specifically to FIG. 1, an initial step 1 involves reading or otherwise obtaining a subject image containing digital imagery data. A subsequent step 2 involves modeling the obtained subject image. Preferably, a three-dimensional model is used to provide a modeled subject image, as indicated as emerging from such step 2.

The purpose of the modeling step is to prepare a subject image and a reference image so that they can be brought into register such that when the reference image is subtracted from the total image the only thing left in the image will be an anomaly or anomalies found in the subject image. The resulting image can be transmitted much more quickly and will require substantially less storage space than would the entire subject image.

The subject image may for example be an X-ray image of a person's thorax. The reference image may be, for example, an X-ray of the same subject's thorax, taken at some earlier time when no anomalies were present. The reference image may also be the X-ray image of a person other than the subject or it may be a computer generated image. Each of the images will be modeled to the same model to prepare them for registration.

FIGS. 7-10 disclose the steps of the modeling process. FIG. 7A shows an X-ray image of a subject's (patient's) thorax, the X-ray image showing ribs 101-106 and a sternum 112.

FIG. 7B shows the basis for the modeling of a 2-dimensional image into a 3-dimensional model approximation of a thorax. The basis for the model can be a three dimensional stack of ellipses 121-129 which are parallel to the horizontal plane and which vary in size and aspect ratio with height so that the ellipse at any height approximates the horizontal cross section of the thorax at that height.

Figure 8:
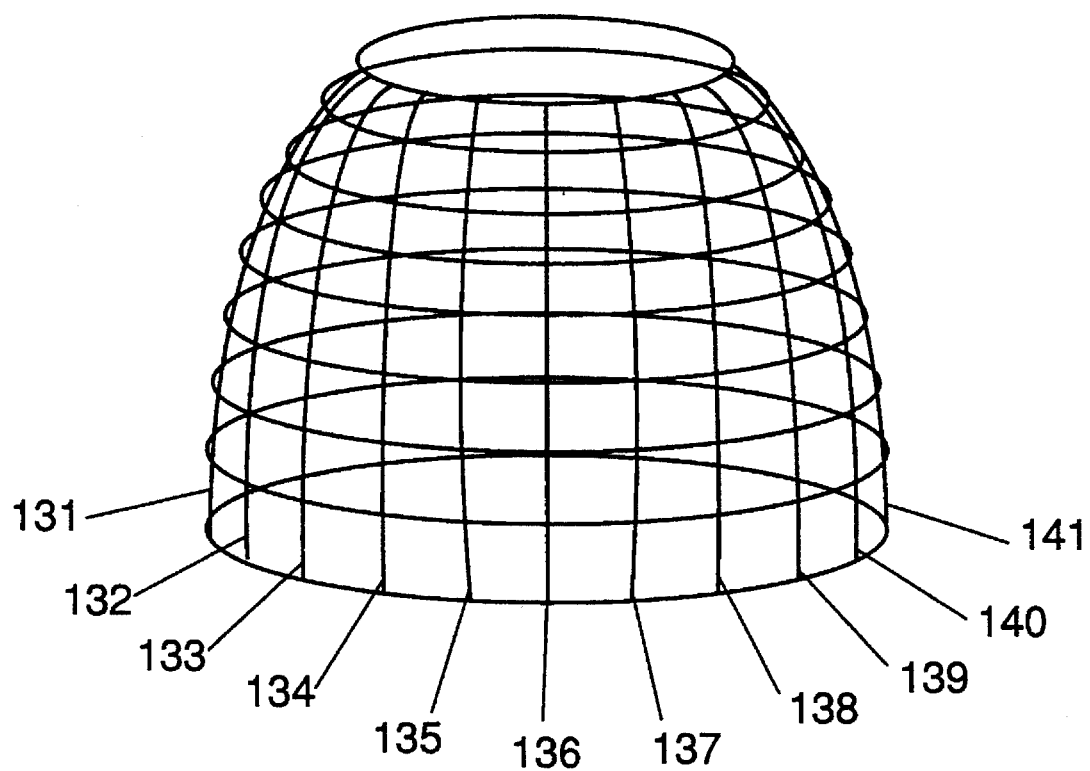

The model can also include three dimensional lines 131-141 which are tangent and perpendicular to each ellipse and which extend downward from the highest ellipse to the lowest ellipse, as shown in FIG. 8. Such lines can be projected onto a 2-dimensional plane in accordance with any 3-dimensional orientation, scale or location of the model.

Figure 9:
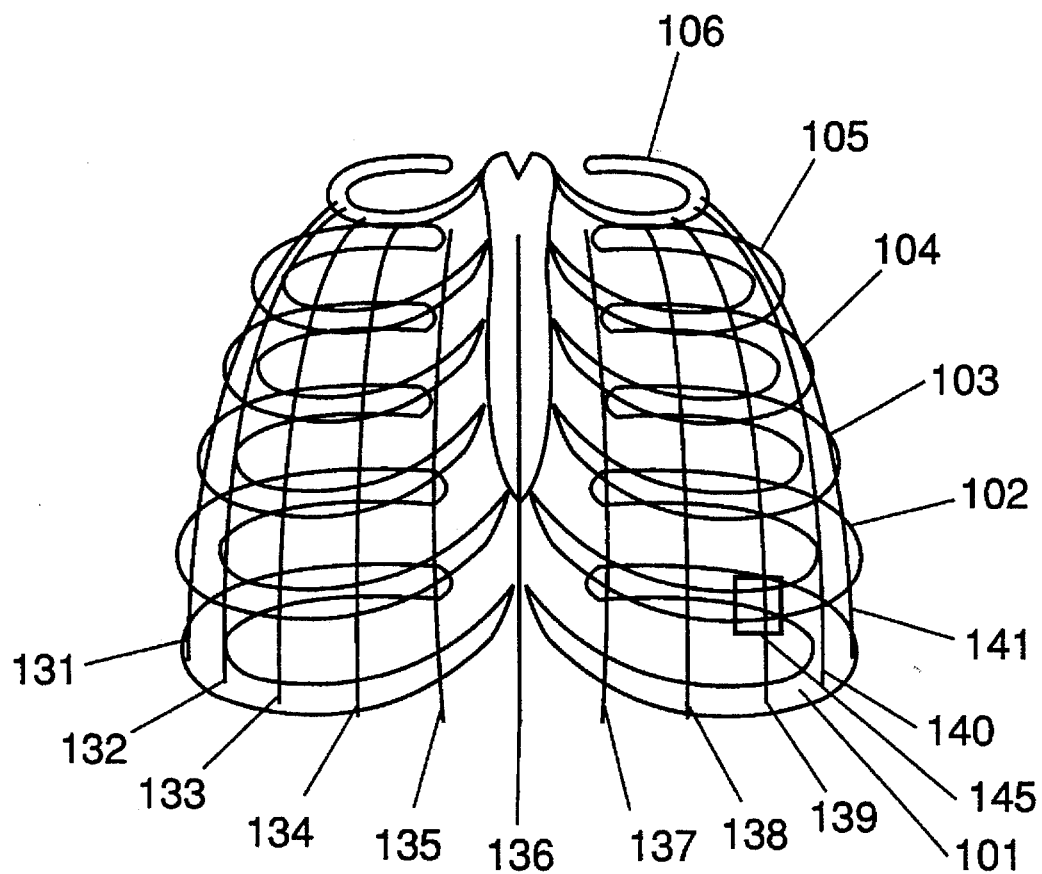

FIG. 9 shows the manner in which the subject image is matched or correlated to the model. A small box, indicated by reference numeral 145 (FIGS. 9 and 10) schematically represents an anomaly or something which is of diagnostic interest. This box is located at the intersection of the line 139 and the rib 102.

Figure 10A:
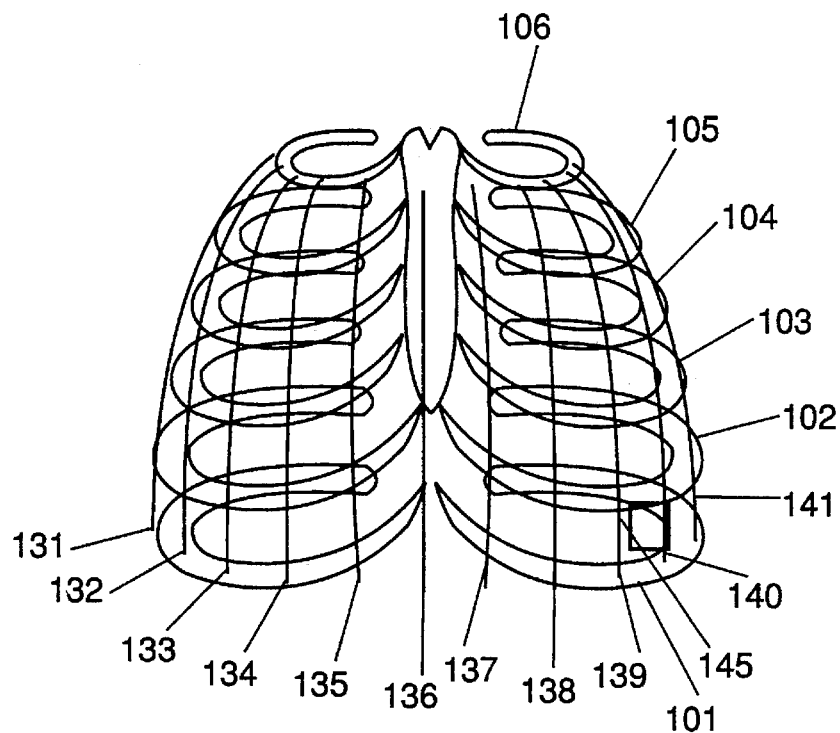
FIGS. 10A and 10B show images of the modeled thorax in slightly different positions.
Figure 10B:
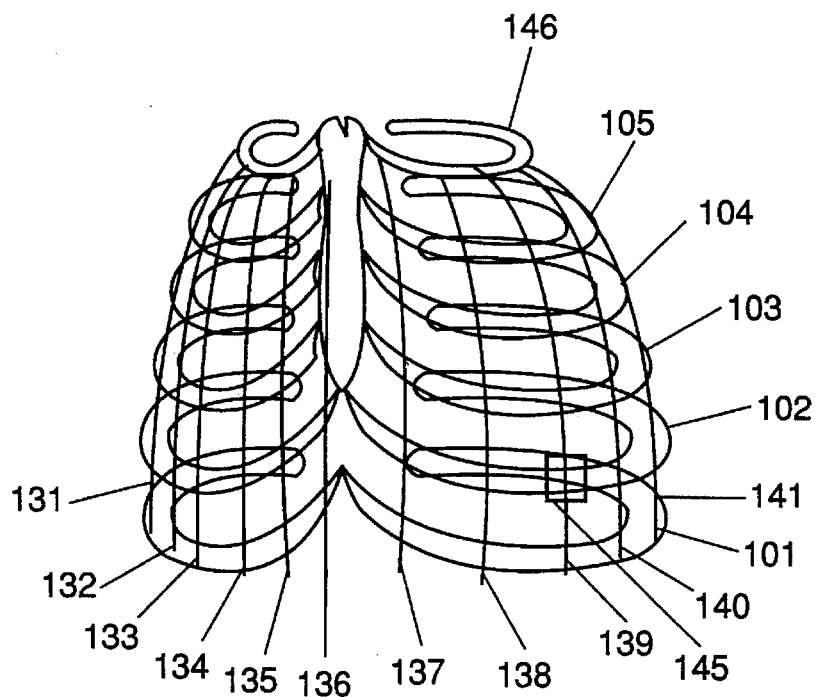

FIGS. 10A and 10B represent the modeled subject image in slightly different poses. Note that the anomaly, indicated by reference numeral 145 is in both poses shown at the intersection of the line 139 and the rib 102.

Therefore, it is possible to identify a number of points throughout the 3-dimensional thorax by relating features in the 2-dimensional thorax image to the projected model. In one possible setting, a grid of control points is created by identifying and indexing all intersections between the ribs 101-112 and the 3-dimensional lines 131-141. These indexed grid points coincide with the same physical features in the image regardless of scale, location or orientation of the thorax in the image. Hence, this grid can be used to correlate images of thoraxes where the thoraxes where the thoraxes are in differing poses.

The modeling of the subject thorax image includes the generation of these grids by the steps:

1. determine the three dimensional location and orientation of the thorax.
2. compute the location and orientation of the three-dimensional model so that its orientation and location are the same as those of the thorax.
3. Generate a projected image of the model superimposed in the thorax.
4. Identify and index the grid of points by finding the intersections between the ribs in the image and the projected lines 131–141.

The reference image is modeled in the same manner as the subject image resulting in a grid for the reference image. Then, using the two grids, the reference image can be registered to the subject image. In this registration the reference image is warped in the two dimensional plane in known ways by fitting the grid of the reference image onto the grid of the subject image.

After the subject image and the reference image have been modeled and registered, the images are differenced. Since the features in the registered images largely coincide, the only difference between them will be the anomaly 145. Thus, if these modeled images are brought into register and the modeled reference image is subtracted from the total image, the only thing left in the image will be the anomaly 145. This remaining image can be compressed more effectively then the original subject image. It can there fore be transmitted much more quickly then the entire subject image and it requires substantially less storage space.

If the remaining image is transmitted to a distant location, the modeled reference image can be added to the transmitted image to obtain the subject image as it originally appeared.

As a more specific example of modeling, assume that someone in the automobile insurance business wished to store or transmit, in accordance with the principles of this invention, digitized imagery representing a large dent in the side of a large, four door sedan. He would have a library of models representing large, four door sedans, small coupes, convertibles, vans, small sedans, etc., representing views of the various vehicles from different angles. Digitized imagery data from a typical large, four door sedan would be modeled to fit the side view model of a large sedan. This modeled reference image would be saved for the time when it became desirable to store or transmit digital imagery of damage to the side of such a car.

The specific car with the dented side would be modeled in the same way to the same model which was used to model the image of the typical large sedan. The modeled images would then be correlated and differenced to leave only imagery concerning the dent. This remaining imagery could then be quickly sent to some distant location where the same library of modeled reference images would be available. The side view imagery of the reference large sedan would be added to the dent imagery to quickly provide a complete image of the damaged car.

Because of the fact that only a small amount of data is transmitted, transmittal time is reduced drastically. Also, much less storage space is needed to store the image resulting from differencing.

A next step involves registration of the modeled subject image with a modeled reference image obtained from modeling a relatively unrelated standard reference image, preferably upon a three-dimensional model. Present FIG. 1 broadly represents such registration in step 3, which as indicated, results in spatial adjustment of images to correct for location, scale, and orientation differences. In other words, the modeled subject image and modeled reference image are translationally correlated, with the resulting correlation of the modeled images in spatial and spectral dimensions.

What emerges from registration step 3 may be referred to as a modeled reference image as well as a registered, modeled subject image, both of which are forwarded to a subtraction step or difference step 4. In such step, the modeled reference image and registered modeled subject image are differenced to form what may be termed a differenced image, which may be subsequently compressed in compression step 5.

In the foregoing exemplary methodology, the subject image may contain medical imagery containing data of relative diagnostic importance. Particularly in connection with such specific methodology, the preferred method may further include interactive editing of the subject image prior to the modeling thereof, so that an area of interest encompassing data of relative diagnostic importance may be specified. Such interactive editing may include viewing of the subject image by an operator with operator designation of the defined area of interest.

Where the subject image includes medical imagery containing data of relative diagnostic importance, the three-dimensional model preferably is representative of a particular element contained in the subject image, with the resulting standard reference image being equivalent to the subject image without the imagery data of relative diagnostic importance.

In addition to the foregoing, the preferred methodology may also include the step of reducing the differenced image prior to compression of such differenced image, so as to provide a reduced differenced image for compression.

It is to be further understood that such methodology may optionally include an additional step of transmitting and/or storing the compressed differenced image for subsequent decompression and reconstitution thereof. Decompression preferably would involve decompressing the compressed differenced image so as to provide a decompressed differenced image. Such reconstitution may comprise combining the decompressed differenced image with the modeled referenced image (or the same information at a remote location) so as to form a reconstituted subject image.

Additionally as to the foregoing exemplary methodology, a standard reference image is preferably adapted to be correlated with subject images originating from more than one image source. Also, a region smoothing operation may be performed to the differenced image to decrease undesired noise therefrom. Separate from immediate transmission of a compressed image, the compressed differenced image may be stored on location or at an intermediate storage location, for subsequent recall and decompression thereof.

In further accordance with another exemplary embodiment of the present invention, a present exemplary method commences with the operation of obtaining a subject image containing data of relative diagnostic importance. As embodied herein and shown for example in FIG. 2, such method 10 begins with a subject image 12 which includes data of diagnostic importance 14. The source of the subject image 12 is not a critical element of the invention. Hence, the invention is applicable to subject images 12 originating from a variety of known digital imagery sources, such as radiography, satellite photography and imaging, etc. The data of relative diagnostic importance 14 can be virtually any information contained in the image desired to be diagnosed for potential analytical purposes.

Figure 2:
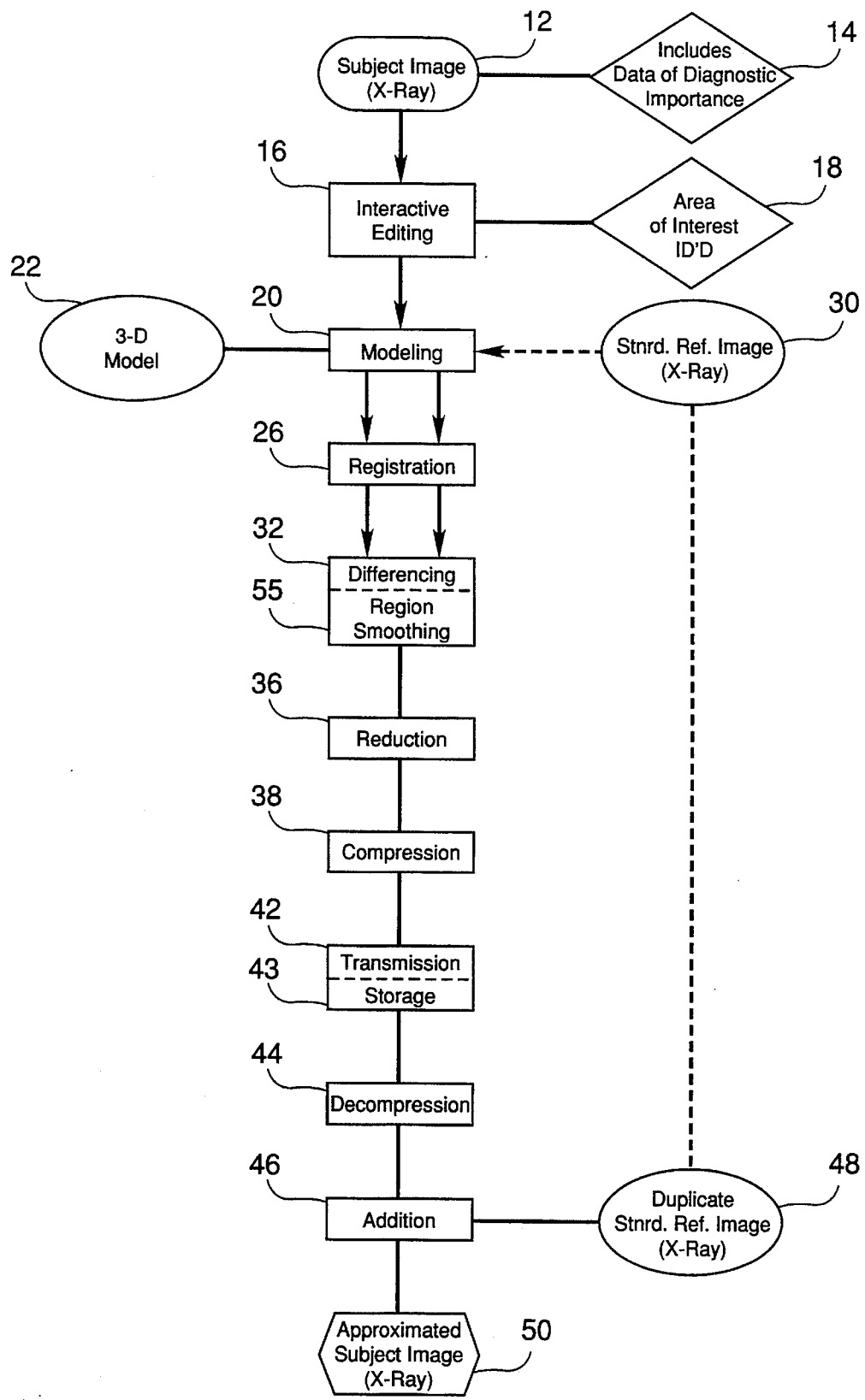
FIG. 2 is a block diagram of another present exemplary embodiment.

Such exemplary method of the present invention preferably further includes interactive editing of the subject image whereby an area of interest is identified, with the area of interest encompassing at least the diagnostically important data. As represented in FIG. 2, interactive editing 36 comprises a method whereby the subject image 12 is designated with an area of interest 18. This can be accomplished by various known means, details of which do not form a particular aspect of this invention. In one preferred embodiment of the invention, editing 36 may be accomplished by direct operator viewing of subject image 12 and designation of an area of interest 18 by any applicable means. In a preferred embodiment, an operator may view the subject image 12 displayed on a CRT screen and designate the area of interest 18 with a light pen. Alternatively, the editing 36 may be accomplished automatically by computer designation of predetermined portions of the subject image 12. Although the area of interest 18 may contain additional data, it should at least contain the data of diagnostic importance 14.

In one alternative embodiment, editing 36 may also include the designation of portions of the subject image 12 which will later be used for registration 26 and modeling functions 20. For example, in the editing of a subject chest X-ray, the operator may directly designate an area of interest which includes the outline of the thorax for use in the modeling step and edges of the spine for use in the registration step. In a preferred embodiment, the operator merely designates the portion of the subject image 12 containing the data of diagnostic importance 14 as the area of interest 18. Preferably, software automatically recognizes the component of the subject image 12 to be used in the modeling process 20 and the registration process 26.

Figure 3:
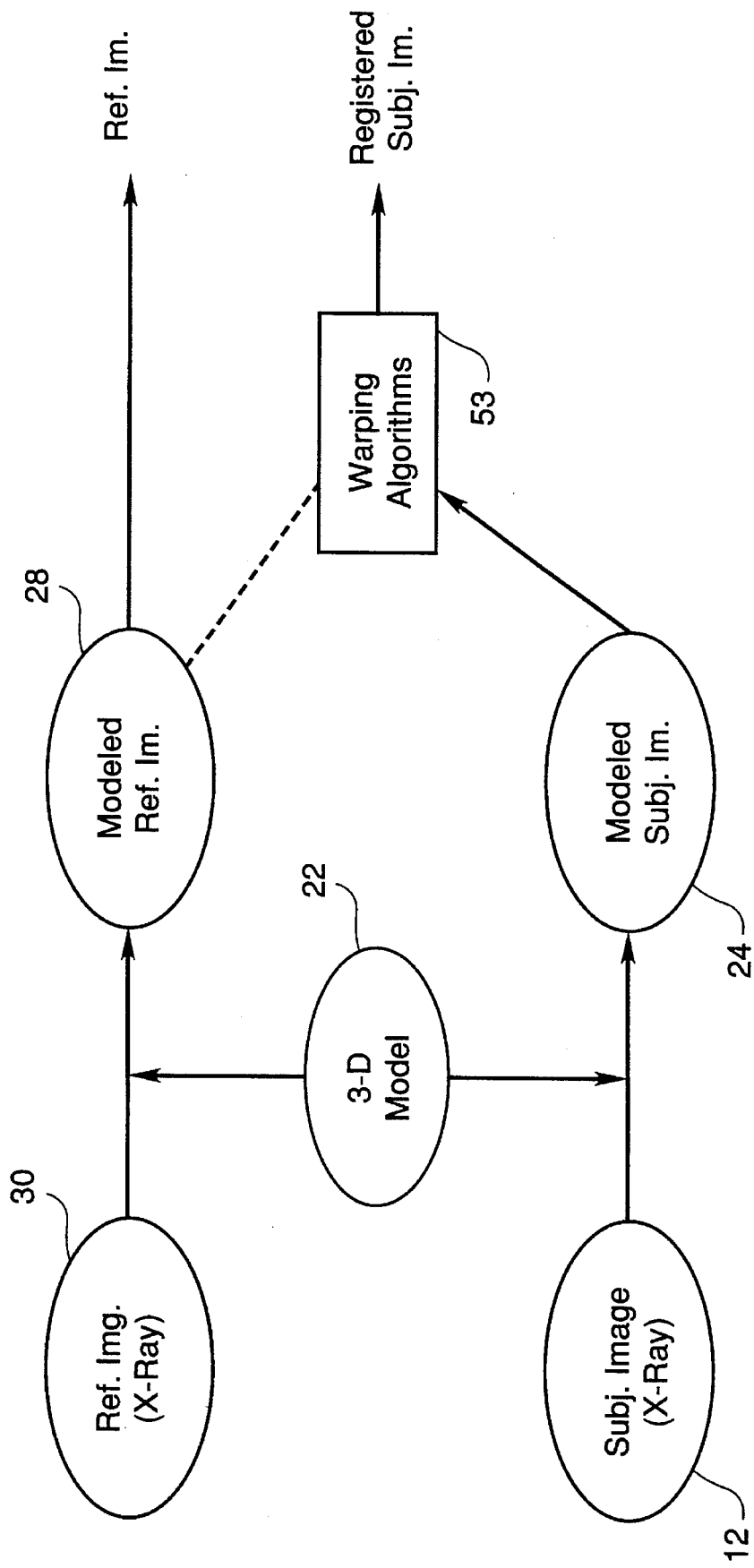
FIGS. 3, 4 and 5 are more detailed block diagrams of certain aspects of the embodiment referenced in present FIG. 2.

As embodied herein and depicted in FIGS. 2 and 3, such exemplary method of the present invention further comprises the operation 20 of modeling the subject image 12 upon a three-dimensional model 22 representative of a particular element contained in the subject image 12 so as to provide a modeled subject image 24. Following the modeling operation subject image is registered to the reference image. Preferably, the registration process 26 comprises an image warping operation 52 as shown in FIG. 3. The image warping operation 52 incorporates image warping algorithms 52 to emulate three-dimensional transformation of a two-dimensional image (subject image 12) into a three-dimensional representation 54 of itself based upon a three-dimensional model 22 and back into a corresponding warped two-dimensional image 57 with reassigned pixel values corresponding to the three-dimensional representation. Such modeling operation 20 provides a modeled subject image 24. Various image warping techniques and algorithms are well known to those of ordinary skill in the art (see for example, prior art patents referenced above); and details thereof need not be discussed herewith for a full understanding and appreciation of the present invention.

The modeling function 20 also correlates the subject image 12 to the model 22 so that the three-dimensional representation 54 "fits" the model 22. The subject image 12 is correlated to the model 22; the model 22 is not correlated to the subject image 12.

The three-dimensional model 22 is a representative model of a particular component depicted in the subject image 12. The model 22 need not be an exact model of the component in the subject image 22, but merely a close enough approximation to allow the warping algorithms for register the subject image 12 to the reference image (30). Thus, it should be understood that the model 22 can be used for subject images 12 originating from various sources and is not restricted to any one subject image 12 originating from any one source. In the preferred embodiment of the invention, the model 22 comprises a computer-generated model of a component element common to the subject image 12 and the reference image 30. For example, the model 22 can comprise a computer-generated model of a human thorax where the subject image 12 constitutes a chest X-ray.

Figure 4:
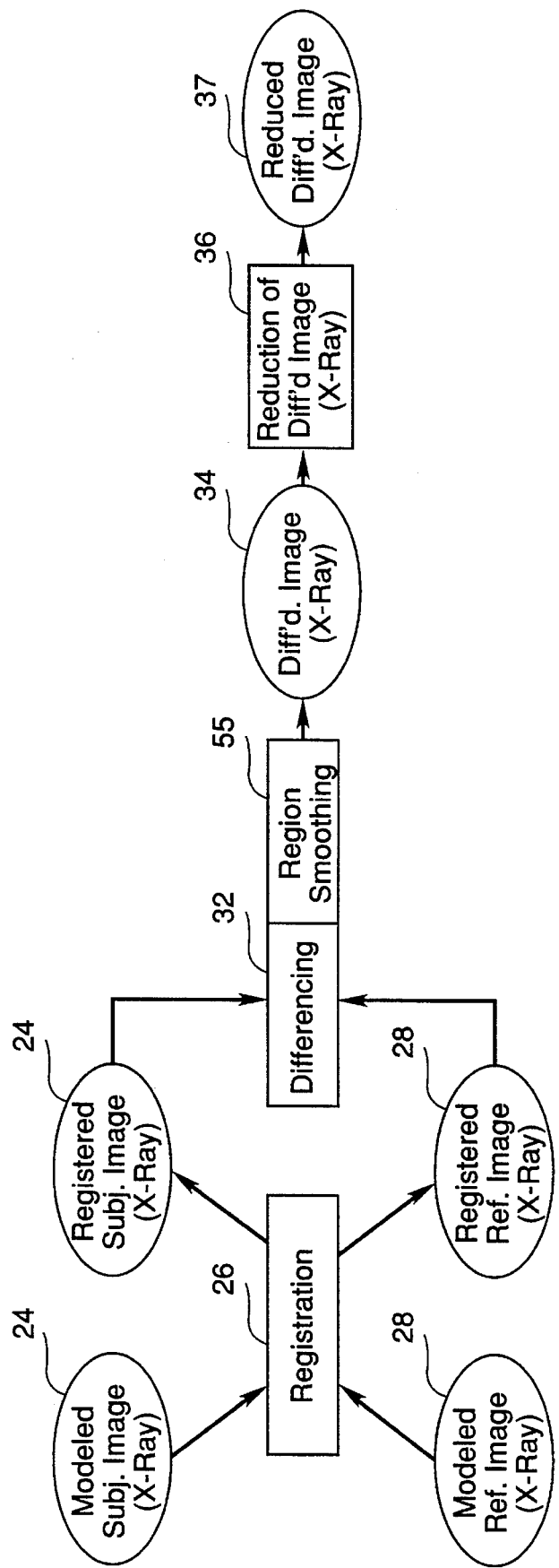

As embodied herein and shown for example in FIGS. 2 and 4, such exemplary method of the present invention further comprises the process of registration 26 of the modeled subject image 24 with a modeled reference image 28. It is well known to those skilled in the art that, prior to subtraction, images preferably should be registered to provide an artifact-free differenced image. Various registration methods themselves are generally well known in the art and any such method (such as edge recognition and comparison or point recognition and comparison) are considered within the scope and spirit of this invention.

The modeled reference image 28 is obtained from the modeling 20 (as described above) of a standard reference image 30 upon the same three-dimensional model 22 that the subject image 12 was modeled upon. It should be understood that, since the subject image 12 and reference image 30 are modeled upon the same common model 22, the resultant modeled subject image 24 and modeled reference image 28 can be translationally correlated, correcting for any orientational and translational disagreement. In other words, there is correlation of modeled images in spatial and spectral dimensions.

The standard reference image 30 is the relative equivalent of the subject image 12 without the data of relative diagnostic importance; in essence, a "healthy" image (such as where patient X-rays are involved). It should be understood that the reference image 30 and subject image 12 need not be related in the time dimension, spectral dimension, or spatial dimension. The method 10 corrects for any differences between the images in such respects. The fact that method 10 (and other present exemplary embodiments of this invention) allows such images to be relatively unrelated is particularly important for applicability of the system in general teleradiology and digital image storage situations. Thus a reference image 30 may be kept on file for repeated use with relatively unrelated "fresh" subject images 12. Additionally, the reference image 30 need not come from the same source as the subject image 12. In one embodiment of the present invention, reference image 30 may be correlated with subject images originating from more than one subject source. For example, in the case of a chest X-ray, a standard reference chest X-ray may used for subject chest X-rays from patient A, B, or C.

As depicted by the dashed lines in FIGS. 2 and 3, the modeling 20 concerning reference image 30 can be accomplished at virtually any time so long as a modeled reference image 28 is provided prior to the differencing operation 32. In a preferred embodiment of the invention, modeling 20 of the standard reference image 30 is accomplished prior to obtaining the subject image 12 and stored for subsequent us with the remainder of method 10. In such manner, additional time need not be expended to generate the modeled reference image 28.

Besides correlating the modeled subject image 24 and modeled reference image 28 in the spatial dimension, the registration process 26 also registers the images in the spectral dimension. Spectral registration is provided to correct for global gray scale differentials existing between the modeled images caused by the use of different equipment, processing methods, time dependent variations in exposure intensity between the images, and the like. Spectral registration ensures that a gray scale difference between the images will not "mask" any true difference. Methods of gray scale transformation and correction are well known in the art and selection and use of any such method is within the scope of this invention. The object of the gray scale or spectral registration is to convert the contrast levels (gray scale value) of one of the modeled images into the value of the other, i.e., to match gray scale values, thereby automatically correcting for contrast differences between the images.

The present invention further includes the process of differencing the modeled subject image and modeled reference image. Forms of digital image differencing for image enhancement have been known in the art for some time and are understood by those skilled in the art. Basically, differencing enhances images by removing contrast detail information which is similar in the images. The information in the differenced image is presumed to be diagnostically (or for other reasons) interesting. The differenced image contains sharply reduced intensity values in the regions where the contrast detail of the original images are similar, and normal intensity values in the regions where the images are appreciably different. Hence, the contrast between this difference information and the background is enhanced. It is understood by those in the art though that when images are differenced, they are not typically compressed. A differenced image which comprises entirely eight bit, low intensity pixels is as large as the image which contains the same number of eight bit pixels, but which displays maximum contrast detail.

As embodied herein and depicted in FIGS. 2 and 4, the method 10 includes the operation 32 of differencing the modeled subject image 24 and modeled reference image 28 so as to provide a differenced image 34. The differenced image 34 comprises noise, some information due to misregistration of the images, and information due to true differences between the images (data 14 of relative diagnostic importance). The differenced image 34 includes at least the previously identified area of interest 18, which encompassed portions of the subject image 12 containing potential diagnostically important data 14. Hence, the method 10 is also useful as a diagnostic tool, since abnormalities in the subject image 12 are amplified in the differenced image 34.

In an alternative embodiment of the invention as embodied herein and shown for example in FIGS. 2 and 4, the method 10 further comprises (optionally) a region smoothing operation 55 to eliminate noise from the differenced image 34. The region smoothing process 55 employs known medium or noise: one embodiment of the present invention makes use of the fact that a difference image can be compressed more efficiently than the high contrast original images, as the system of the present invention applies a compression algorithm to the difference image, which algorithm includes the step of image segmentation to reduce fluctuation of the image function in the difference image and thereby allow greater compression ratios. Application of such potent compression algorithms to the difference image rather than the subject image reduces the artifacts which such algorithms often cause.

One method of the present invention further optionally comprises the operation of reduction of the differenced image to provide a reduced differenced image which includes at least the previously identified area of interest. The differenced image is reduced by removing portions of information therefrom that will still be contained in the final image but which will come from the reference image. Therefore, the final image will appear "whole" even though only a portion of the subject image was actually compressed.

As embodied herein and depicted for example in FIGS. 2 and 4, the method 10 may include reduction operation 16. In reduction 16, the differenced image 34 is edited or "trimmed" of the portions outside the previously identified area of interest 18. Various known conventional means can be utilized to so reduce the differenced image 34. Preferably, an editing program or the like is used to automatically eliminate portions of the differenced image outside the area of interest 18, with such "eliminated" portions being subsequently replenished such as from the standard reference image or data. In an alternative embodiment, an operator can designate which portions of the differenced image 34 are to be eliminated. The concept of reduction operation 16 of the differenced image 34 is not crucial to the spirit of the invention and can be accomplished in any known applicable manner.

The foregoing exemplary method of the present invention may further optionally comprise the feature of enhanced compression of at least the area of interest of the reduced differenced image. The broad concept of compression per se of digital imagery is widely known in the art and need not be explained here in detail for a full and adequate understanding of this invention. Practice of the present invention, however, greatly enhances the effectiveness of even such conventional compression operations beyond the prior achievements of such conventional methods operated by themselves. By applying known compression algorithms to the reduced differenced image, the invention exploits the fact that such algorithms are more efficient at compressing images with a lower dynamic intensity range.

For example, a typical X-ray image has an expected dynamic intensity range of values from 0 to 255, which requires 8-bit units to store the data. Differencing may reduce the expected range to less than 0 to 64, which requires 6-bit units to store the data, thereby reducing the total amount of data contained in the image. Secondly, practice of the present invention allows for reduction of the difference image file to an identified region of interest, thereby greatly reducing the amount of data to be subsequently compressed. Thirdly, the invention exploits the fact that compression of a differenced image results in less severe artifacts being generated by the compression algorithms. Hence, stronger compression tools can be used on a differenced image without sacrificing reliability.

Figure 5:
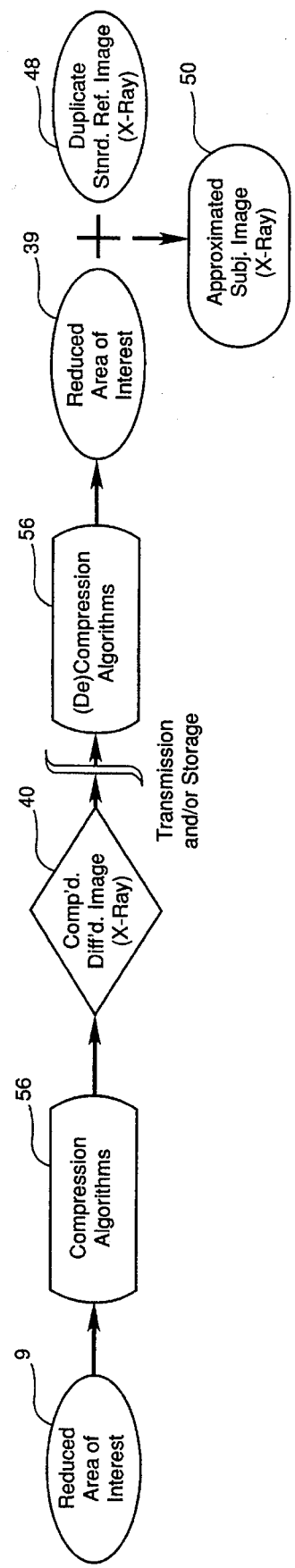

As embodied herein and shown for example in FIGS. 2 and 5, method 10 preferably includes the process of enhanced compression 38 of at least the area of interest from the reduced differenced image 39 so as to provide a compressed differenced image 40. In the exemplary preferred embodiment of the invention as shown in FIG. 5, compression 38 is accomplished with conventional compression algorithms 56, with practice of the overall method 10 resulting in more efficient use of such algorithms 56, as explained above.

The foregoing exemplary method of the present invention further optionally includes the step 42 of transmission of the compressed differenced image to a predetermined receiving station whereby the compressed area of interest can be subsequently decompressed for addition to a duplicate of the standard reference image. Transmission can be accomplished by conventional known means, for example, via 9600 baud telephone lines. Due to the enhanced compression and increased compression ratios, the time required for transmission is greatly reduced as compared to conventional methods.

As embodied herein and shown for example in FIGS. 2 and 5, such exemplary method 10 includes the optional step of transmission 42. In such preferred embodiment of the invention, standard 9600 baud telephone lines are utilized whereby the compressed difference image 40 is transmitted to a desired receiving station (which may be an "end" destination or an intermediate storage location from which subsequent transmission to an "end" station is made). The only requirement for the receiving station (if it is an "end" station at which reproduction is desired) is that it have a duplicate 48 of the standard reference image 30 for addition 46 to the decompressed reduced area of interest 39, and that it have the applicable hardware/software to perform decompression 44 and addition 46. Preferably, the receiving station is in possession of the duplicate reference image 48 well ahead of the expected transmission time.

Decompression 44 may be accomplished with conventional (de)compression algorithms 56 (see FIG. 5). Decompression 44 is a widely known technique to those skilled in the art. The addition process 46 comprises the operation of combining the duplicate reference image 48 with the decompressed area of interest 39. This results in an approximated (or reconstructed) subject image 50 which is a relatively precise approximation of the original subject image 12. The portions of the differenced image 34 eliminated by the reduction process 16 are present in the approximated image 50 since they are never eliminated from the duplicate reference image 48. In essence, the approximated subject image 50 represents a complete picture composed of the area of interest 18 of the subject image 12 and with the reference image 30 comprising the remainder of the picture.

Storage of digital images can be quite expensive, requiring vast storage space. Due to the enhanced compression achieved with the present invention, storage requirements are greatly reduced. In a preferred embodiment of the invention as shown in FIGS. 2 and 5, the method 10 further optionally includes an enhanced intermediary storage capability whereby the compressed differenced image 40 can be stored and repeatedly recalled for subsequent decompression 44. Any conventional means for storing digital data can be employed. For example, the image 40 can be stored on magnetic tape, storage disc, etc. Such storage function 43 can exist at the transmitting station, the receiving station, or at an intermediary station.

In further accordance with the present invention, the foregoing method is provided for the effective compression and transmission of radiographic imagery exploiting prior known information of the image. The following briefly overviews an exemplary present process specifically in the context of X-rays. As embodied herein and shown for example in FIGS. 2 through 5, a subject X-ray 12 comprising data of relative diagnostic importance 14 is obtained. The subject x-ray 12 undergoes interactive feature identification 36 to identify features for use in the modeling operation.

The modeling operation 20 incorporates image modeling procedures to generate of three-dimensional representation 54 of the subject X-ray 12 based upon a computer-generated three-dimensional model 22 representative of a particular element contained in the subject X-ray 12.

A standard reference X-ray 30 is modeled according to the same process 20, and upon the same computer-generated three-dimensional model 22, to provide a modeled reference X-ray 28. The standard reference X-ray 30 is the relative equivalent of the subject X-ray 12 without the diagnostically important data 14.

The modeled reference X-ray 28 and modeled subject X-ray 24 then undergo the registration process 26, and then undergo a differencing operation 32. The differenced X-ray 34 may then undergo reduction 16, followed by compression 38.

The compressed differenced X-ray 40 is then subjected to either a transmission operation 42 or storage operation 43 for recall and later use. In either event, during any subsequent decompression operation 44, a duplicate standard reference X-ray 48 is used to form an approximated subject X-ray 50.

Figure 6:
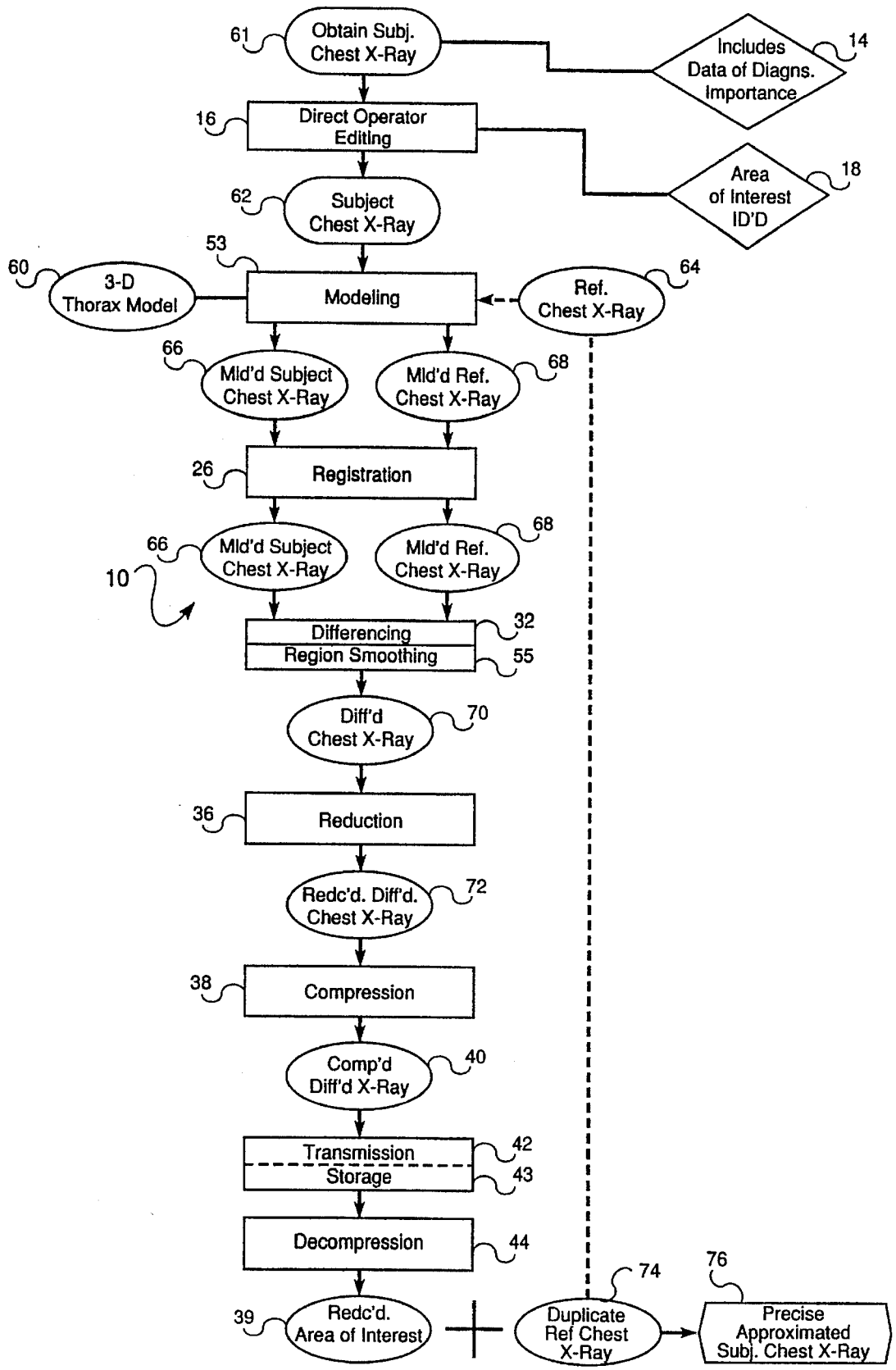
FIG. 6 is a block diagram of yet another exemplary preferred embodiment of the present invention.

An exemplary embodiment of the present invention directed more specifically to the compression and transmission of chest X-rays is depicted in FIG. 6. A subject chest X-ray 61 comprising data of relative diagnostic importance 14 is obtained. The subject chest X-ray 61. undergoes a process of interactive feature identification 36 whereby the operator identifies features for use in the modeling procedures.

The subject chest X-ray 61 is then subjected to a modeling process. Although not specifically designated in FIG. 6 such modeling process is preferably the equivalent of the modeling process depicted in FIGS. 2 and 3. Some time prior to modeling of the subject chest X-ray 61, a relatively unrelated standard reference chest X-ray 64 modeled according to the same process used on the subject chest X-ray 64, and upon the same computer-Generated three-dimensional thorax model 60, so as to provide a modeled reference chest X-ray 68. The standard reference chest X-ray 64 is the relative equivalent of the subject chest X-ray 61 without the diagnostically important data 14. Following the modeling process the subject image undergoes a registration process, which registration process incorporates image warping algorithms 53 to spatially correct the subject image eliminating spatial differences between subject and reference images.

The reference chest X-ray 68 and registered subject chest X-ray 66 then undergo a differencing operation 32 and region smoothing operation 55 so as to provide a differenced chest X-ray 70. At a minimum, the differenced chest X-ray 70 includes the previously identified area of interest 18 which encompasses at least the data of diagnostic importance 14.

The differenced chest X-ray 70 then undergoes a reduction process 16 to provide a reduced differenced chest X-ray 72. The reduction process 16 eliminates unwanted portions of the differenced chest X-ray 70 with the reduced differenced chest X-ray 72 comprising at a minimum the area of interest 18.

At a minimum, the reduced area of interest 39 of the reduced differenced chest X-ray 72 then undergoes a compression process 38. The compression process 38 utilizes compression algorithms to produce a compressed differenced chest X-ray 40.

The compressed differenced chest X-ray 40 is then subjected to a transmission operation 42 whereby the chest X-ray 40 is transmitted to a receiving station. Optionally, the compressed differenced chest X-ray 40 may undergo storage 43 at the same or a remote location for recall and later use. At the receiving station, the compressed differenced chest X-ray 40 undergoes decompression 44 so as to provide at least the reduced area of interest 39. The reduced area of interest is then combined with a duplicate standard reference chest X-ray 74 to provide a precise approximated subject chest X-ray 76.

It should be apparent to those skilled in the art that various modifications and variations can be made in the method of the present invention without departing from the scope and spirit of the invention. Likewise, it will be understood that the foregoing language is by way of example only, and is not intended as limiting broader present features and aspects. Thus it is intended that the present invention cover the modifications and variations of this invention provided they come within the scope of the appended claims and their equivalents.

What is claimed is:

1. A method for the processing of digital imagery data, comprising the steps of:

modeling a two-dimensional subject image into a three-dimensional model in digital electronic form to provide a modeled subject image, said subject image being data produced in a two-dimensional field by a digital data collection system;

providing a relatively unrelated standard reference image in digital electronic form modeled into said three-dimensional model in digital electronic form to provide a modeled reference image, said relatively unrelated standard reference image being adapted for correlation with subject images originating from more than one image source;

performing registration of said modeled subject image with said modeled reference image to translationally correlate said images in spatial and spectral dimensions;

differencing said modeled reference image and said modeled subject image to retain the differences between said images;

transmitting the differences between said images to a predetermined receiving station for processing and/or storage thereat, wherein the differences between said images can be subsequently processed or recalled for addition to a duplicate of said relatively unrelated standard reference image to achieve an approximation of said original subject image.

2. A method as in claim 1, wherein said subject image contains medical imagery containing data of relative diagnostic importance; and said method further includes interactive editing of said subject image prior to modeling thereof so that an area of interest encompassing data of relative diagnostic importance is specified.

3. A method as in claim 2, wherein said interactive editing includes viewing of said subject image by an operator and operator designating of said area of interest.

4. A method as in claim 1, wherein: said subject image includes medical imagery containing data of relative diagnostic importance;

said three-dimensional model is representative of a particular element contained in said subject image; and said standard reference image is equivalent to said subject image without said imagery data of relative diagnostic importance.

5. A method as in claim 1, further including the steps of reducing said differenced image and then compressing said differenced image to provide a reduced and compressed differenced image.

6. A method as in claim 5, further including the steps of:

decompressing said compressed differenced image so as to provide a decompressed differenced image; and combining said decompressed differenced image with said modeled reference image so as to form a reconstituted subject image.

7. A method as in claim 1, wherein said modeling step comprises an image warping operation incorporating image warping algorithms, said image warping operation emulating three-dimensional transformation of said subject the orthogonal projection of which is the two-dimensional image whereby said two-dimensional image is registered to a reference image.

8. A method as in claim 7, wherein said three-dimensional model comprises a computer-generated model of a component element common to said subject image and said reference image.

9. A method in claim 1, further comprising applying a region smoothing operation to said differenced image to decrease undesired noise therefrom.

10. A method for compression of radiographic imagery, said method comprising:

modeling a two-dimensional subject X-ray into a three-dimensional model in digital electronic form representative of a particular element contained in said subject x-ray, so as to provide a modeled subject x-ray; said subject X-ray being electronic data produced in a two-dimensional field by a digital radiographic collection system, said subject X-ray being interactively edited to identify an area of interest;

obtaining a modeled reference X-ray by modeling a relatively unrelated standard reference X-ray upon said three-dimensional model, said standard reference X-ray being a substantial equivalent of said subject X-ray without the diagnostically important data and being adapted for correlation with subject X-rays originating from more than one image source;

registering said modeled subject X-ray and modeled reference X-ray so they are translationally correlated for correlation thereof in spatial and spectral dimensions;

differencing said modeled reference X-ray and said modeled reference X-ray subsequent to said registration thereof, to provide a differenced X-ray including at least said previously identified area of interest;

compressing at least said area of interest of said differenced X-ray to provide a compressed differenced X-ray;

transmitting said compressed differenced X-ray to a predetermined receiving station and optionally storing same thereat, so that said compressed area of interest can be subsequently decompressed for addition to a duplicate of said relatively unrelated standard reference X-ray to achieve at said receiving station an approximation of said subject X-ray, which approximation is true to said subject image in a designated area of interest.

11. A method as in claim 10, further including the steps of decompressing said compressed differenced X-ray and adding such decompression to a duplicate of said standard reference X-ray so as to reform at a relatively remote location a representation of said subject X-ray with relative duplication of said identified area of interest thereat.

12. A method as in claim 10, further including the step of reducing said differenced X-ray prior to compression thereof.

13. A method as in claim 10, wherein said modeling step includes an image warping operation incorporating image warping algorithms, said image warping operation emulating three-dimensional transformation of a two-dimensional image into a three-dimensional representation of itself based upon said three-dimensional model and transformation back into a corresponding warped two-dimensional image.

14. A method as in claim 10, wherein:
said three-dimensional model comprises a computer-generated model of an X-ray of a human thorax; and
said subject X-ray comprises a chest X-ray and said standard reference X-ray comprises a "healthy" chest X-ray without diagnostically important data.

15. A method as in claim 10, further comprising storing said compressed area of interest of said differenced X-ray for subsequent recall and decompression thereof.

16. A method for the compression and transmission and/or storage of a chest X-ray containing diagnostically important data, which method reduces transmission time and storage requirements by exploiting prior known information about such chest X-ray, said method comprising the steps of obtaining a subject chest X-ray, said subject chest X-ray containing data of relative diagnostic importance;

interactive direct operator editing of said subject chest X-ray wherein an operator identifies an area of interest of said subject chest X-ray which includes at least said diagnostically important data;

modeling said subject chest X-ray upon a computer-generated three-dimensional model of a human thorax to obtain a modeled subject chest X-ray;

registering through an image warping operation said modeled subject chest X-ray with a previously obtained modeled reference chest X-ray, such being obtained by modeling a relatively unrelated standard reference chest X-ray based upon said computer-generated model of a human thorax, said standard reference chest X-ray being a relative equivalent of said subject chest X-ray without said diagnostically important data and adapted for correlation with subject X-rays originating from more than one image source, wherein by said registering said modeled subject chest X-ray and said modeled reference chest X-ray are translationally correlated, for resulting correlation of said X-rays in spatial and spectral dimensions;

differencing said modeled reference chest X-ray and said modeled subject chest X-ray subsequent to said registering step, to provide a differenced chest X-ray including at least said previously identified area of interest;

reducing said differenced chest X-ray to provide a reduced differenced chest X-ray including at least said area of interest;

performing enhanced compression of said area of interest of said reduced differenced chest X-ray, using compression algorithms, to provide a compressed differenced X-ray; and transmitting said compressed differenced X-ray to a predetermined receiving station for processing and/or storage thereat, wherein said compressed differenced X-ray can be subsequently processed to be decompressed for addition to a duplicate of said reference chest X-ray to achieve an approximation of said original subject chest X-ray which approximation is true to said original subject image in a designated area of interest.

* * * * *